US00PP09298P

United States Patent [19]

Fukuda

[11] Patent Number: Plant 9,298

[45] Date of Patent: Sep. 26, 1995

[54] APPLE TREE 'TENSEI'

[75] Inventor: Satoru Fukuda, Itayanagi, Japan

[73] Assignee: Fukushima Tenkoen Co. Ltd., Fukushima, Japan

[21] Appl. No.: 238,062

[22] Filed: May 3, 1994

[51] Int. Cl.[6] ..... A01H 5/00

[52] U.S. Cl. ..... Plt./34.1

[58] Field of Search ..... Plt./34.1

*Primary Examiner*—James R. Feyrer

*Attorney, Agent, or Firm*—Limbach & Limbach; W. Patrick Bengtsson

[57] ABSTRACT

The present invention relates to a new and distinct variety of apple tree originating as a bud mutation of "Fuji", the Japanese leading late maturing apple cultivar. The new apple tree is generally similar to its parent, "Fuji", with respect to spreading tendency, medium vigor, length of internode, but it is distinguished from "Fuji" by larger size of fruit, leaf, opened flower than its parent.

6 Drawing Sheets

BACKGROUND OF THE INVENTION

The present invention relates to a new and distinct variety of apple tree which was discovered as a limb mutation of known "Fuji" variety. "Fuji" is a late maturing variety of apple tree, which is picked in November to December. In comparison to "Fuji", the fruit of the apple tree of this invention is large or very large and contains much more fruit juice. In addition, the leaves and opened flowers of the apple tree of this invention are larger than that of the parent tree.

It is anticipated that these large or very large sized fruit will be more attractive to most segments of the consuming public from the standpoint of size and quality appeal, as compared to its parent "Fuji". The new variety has been named "Tensei". The genus and species of the new variety is *Malus pumila* Mill.

The new variety of apple tree has been repeatedly asexually reproduced by placing buds of "Tensei" on mature tree of other varieties. Such asexual reproductions have run true to the original discovery in every distinguishing respect by producing the large or very large sized fruit, leaf and opened flower described herein, to establish that the variety is stable.

SUMMARY OF THE VARIETY

The new variety of apple tree of this invention, "Tensei", is a bud mutation of the known "Fuji" apple tree variety. "Tensei" in general is similar to "Fuji" with respect to spreading tendency, medium vigor and medium internode, but is distinguished from "Fuji" because it develops large or very large sized fruit that contains large amounts of juice. In addition, the leaves and opened flowers of the apple tree of this invention are larger than of those of the parent "Fuji" tree.

The following is a detailed description of this new "Tensei" variety of apple tree.

DESCRIPTION OF THE INVENTION

Figure 1:
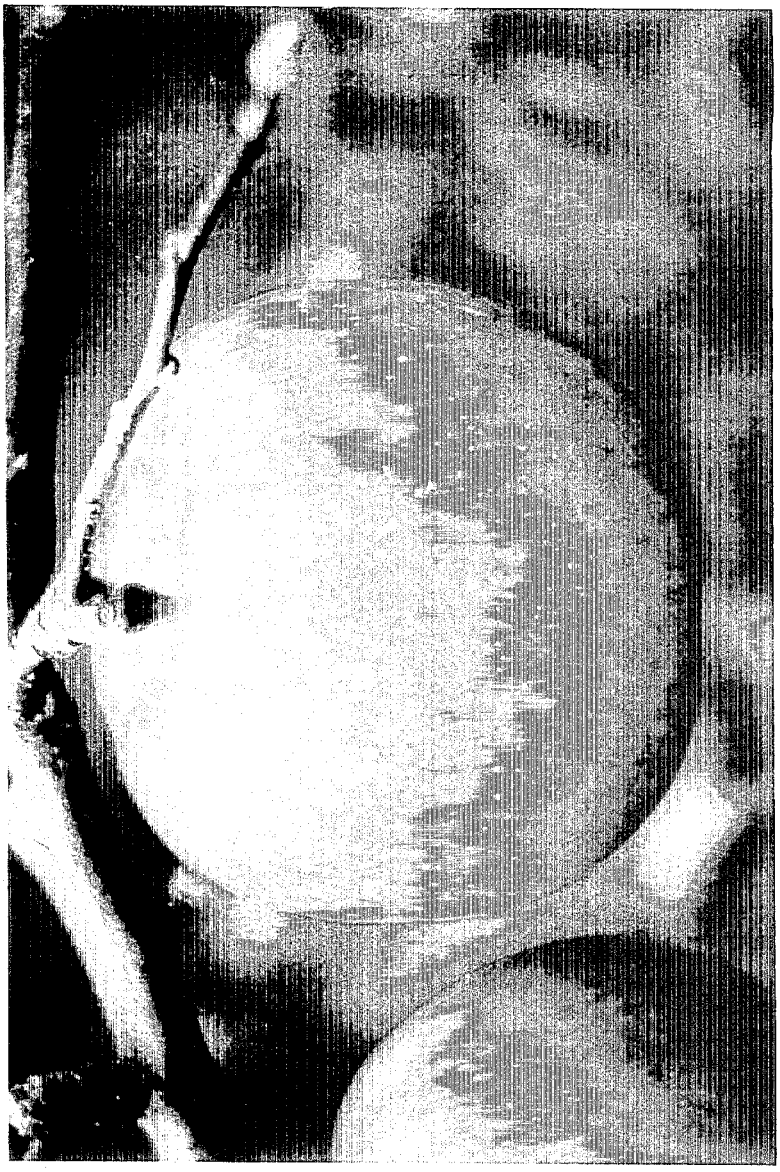
FIG. 1 is a photograph of "Tensei" apple on the original limb.
Figure 2:
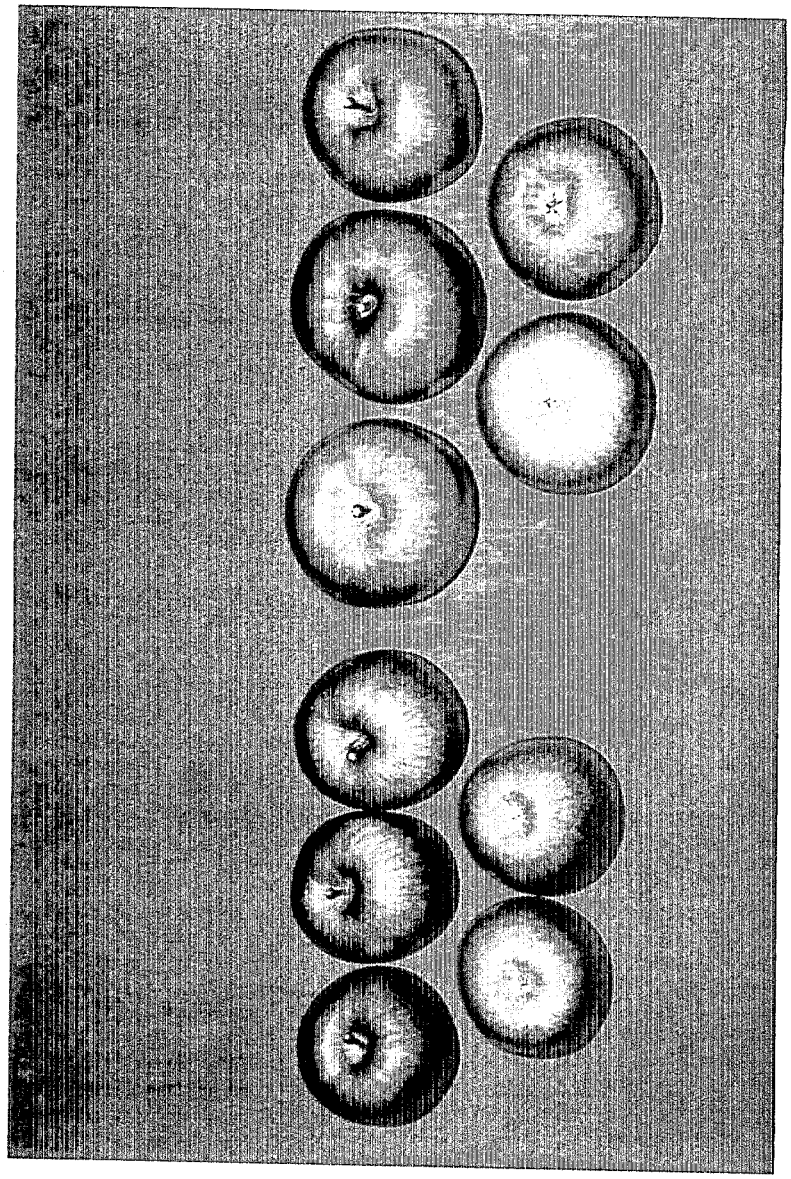
FIG. 2 is a photograph of "Tensei" apples (5 apples on the right side) compared to "Fuji" (5 apples on the left side).
Figure 3:
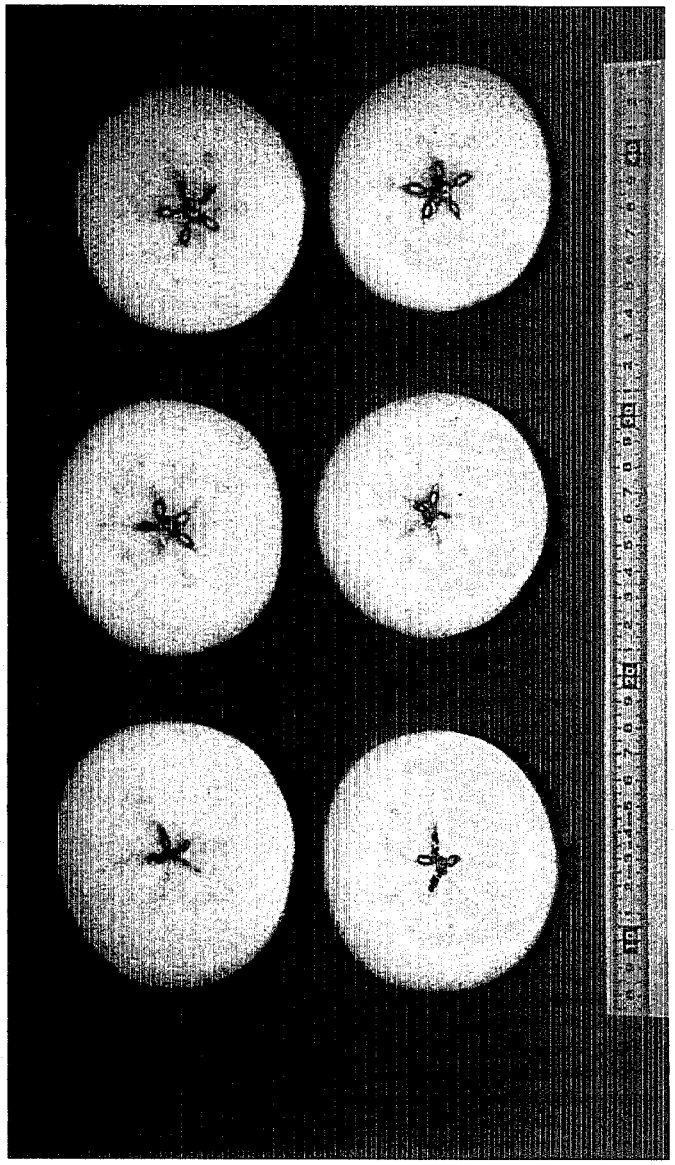
FIG. 3 is a photograph of a cross section of "Tensei" apple (middle) compared to "Fuji" (right) and "Hokuto" (left).
Figure 4:
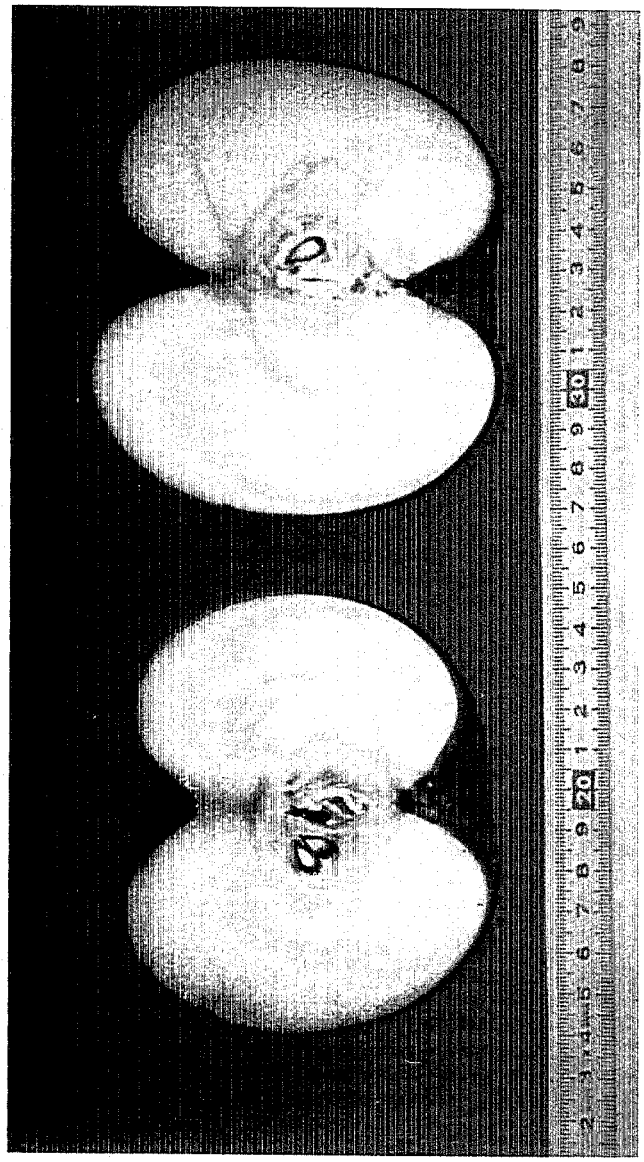
FIG. 4 is a photograph of a longitudinal section of a "Tensei" apple.
Figure 5:
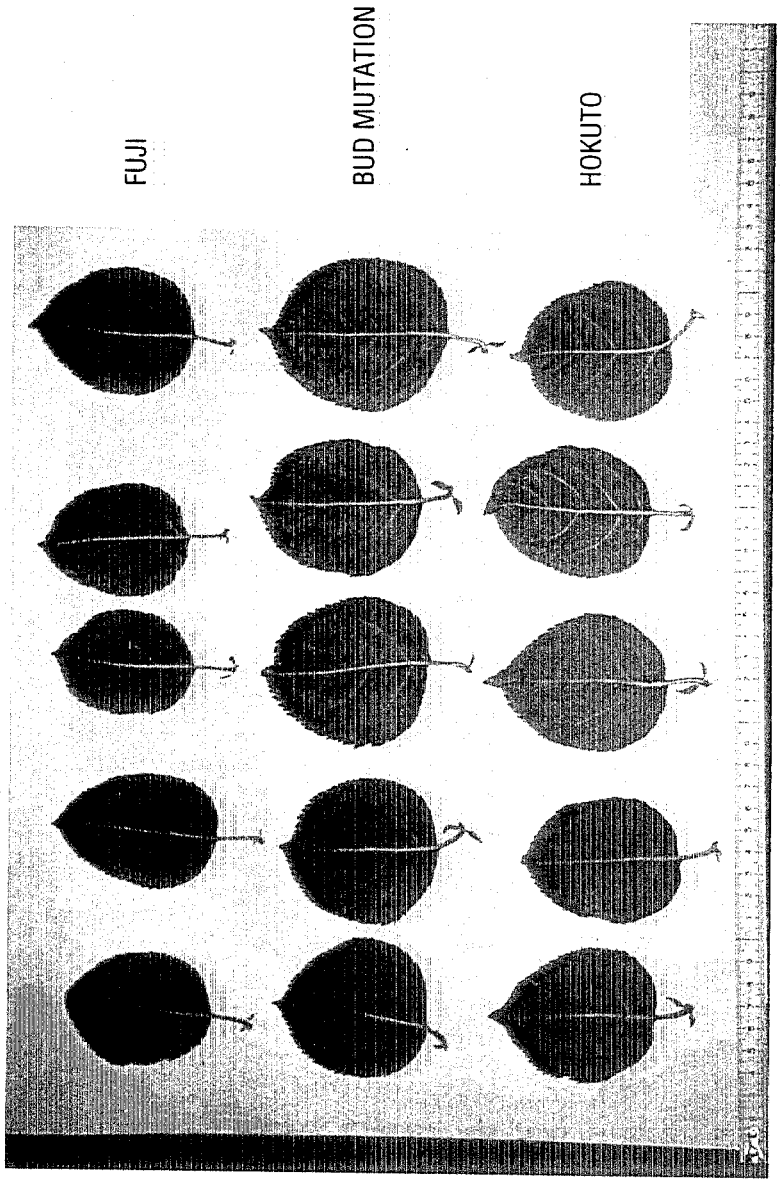
FIG. 5 is a photograph of leaves of "Tensei" (middle) compared to "Fuji" (top) and "Hokuto" (bottom).
Figure 6:
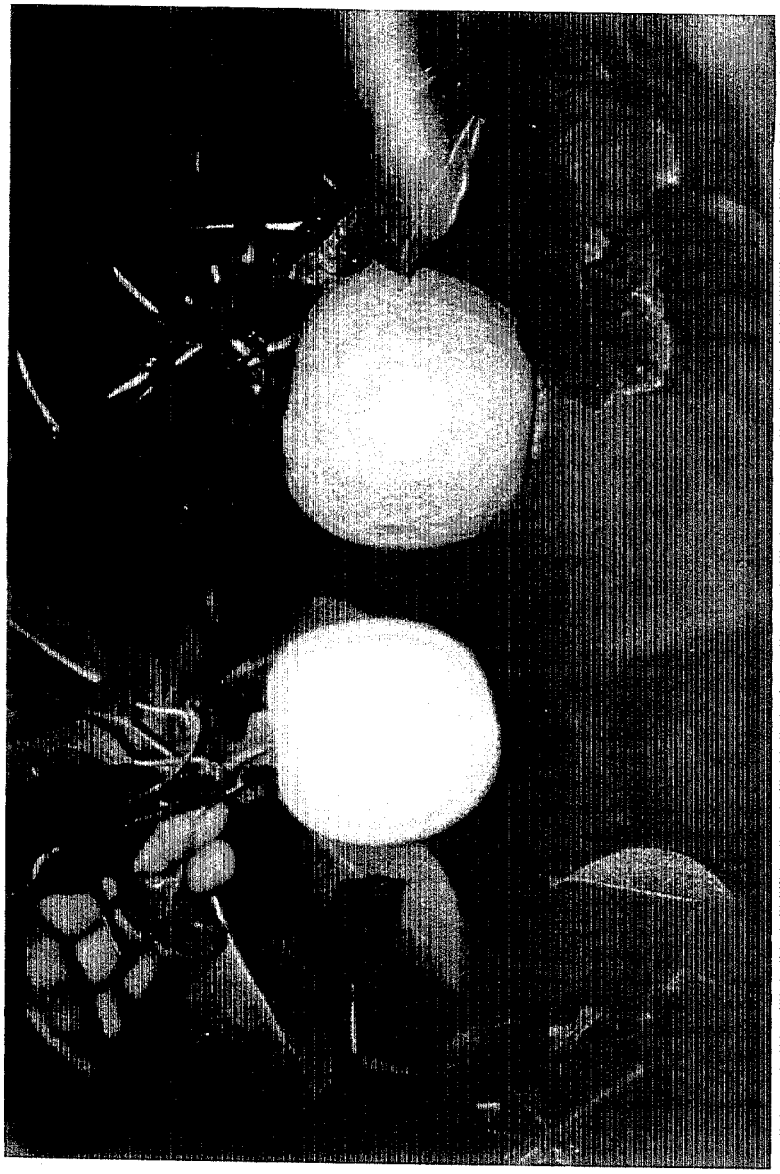
FIG. 6 is a photograph of "Tensei" fruit (right) compared to "Fuji" fruit (left) on 70 days before the harvest time.

In November, 1986, the inventor discovered an apple tree branch with some large sized fruit compared with "Fuji". This branch appeared to be a budwood of the mutation on an approximately 25-year old original "Fuji" tree and was found in his orchard, located at Itayanagi-machi, Kitatsugaru-gun, Aomori prefecture, Japan. In 1987, he was convinced that this branch was a new bud mutation of "Fuji", and confirmed that it was distinguished from its parent "Fuji" according to the characteristics of the size of the fruit, opened flower and leaf. The size of the fruit, opened flower and leaf of the tree of this variety were larger than that of the parent tree "Fuji." In addition, the fruit of this variety had an excellent taste and was good in quality.

The inventor has been practising continuous observation of the originally discovered apple tree and examination of the characteristics of the apple variety, since November, 1986, in his orchard, located at Itayanagi-machi, Kitatsugaru-gun, Aomori prefecture, Japan. In May, 1988, in order to confirm the stability of the mutation by cultivation, the inventor grafted the budwoods of the mutation onto the "Fuji" apple tree in the inventor's orchard.

In addition the inventor has been bringing up two stubs of the grafted tree and 19 stubs of tree of the variety, to investigate the characteristics of the variety and the stability of the bud mutation.

In May, 1989, Atushi Okada, an apple grower in Fukushima Tenkoen Co., Ltd., observed the original sport and grafted bud mutation, and confirmed that it had a opened flower whose size was much larger than that of the parent tree "Fuji", and finally confirmed that it was basically obtained by not grafting some branch onto the original "Fuji", but instead by a bud mutation of "Fuji" variety.

In August and November, 1989, Atushi Okada also confirmed the stability of the characteristics of the new apple variety which developed very large sized fruit, and leaves compared with that of the parent tree "Fuji".

In 1990, a fruit was first ripened on the branch grafted in May, 1988, and it was confirmed that it was a new variety of apple tree because it had the same characteristics as the originally discovered fruit of the new variety and was stable.

In addition the inventor investigated the characteristics of the new variety, by analyzing about 40 fruits harvested from the original tree, every year from November, 1989 to November, 1990.

The following is a description of the characteristics of the new variety of apple tree of this invention.

Tree: The size of the tree is medium size, and habit of branches of the tree is spreading tendency, and vigor of the tree is medium.

Shoot: Thickness of the one-year-old shoot is stout, and size of lenticels of the one-year-old shoot is medium, and number of lenticels of the one-year-old shoot is much (numerous) as compared to that of the parent tree "Fuji". Length of internode of the one-year-old is medium. Predominance of axillary flower bud of this tree is medium.

Leaves: L/B ratio of leaf of this tree is rounded, serrations of leaf is serrate, length of lamina of this tree is approximately 7.86 cm ("Fuji": 8.11 cm), and width of leaf of the tree is approximately 6.41 cm ("Fuji": 5.52 cm). Color of leaf is dark green, and size of stipules of leaf is larger than that of the parent tree "Fuji". Length of petiole is short, and thickness of petiole is medium.

Flower: Size of opened flower of this tree is large (larger than that of the parent tree "Fuji") and color of unopened flower of this tree is purplish pink.

Fruit:

*Shape.*—Shape of fruit of this tree is round, crowning at eye end of the fruit is medium, aperture of eye of the fruit is open, depth of basin of the fruit is medium, breadth of basin of the fruit is broad, depth of stalk cavity of the fruit is broad, size of the fruit is very large (average weight: 496 g, larger than that of the parent tree "Fuji").

*Color.*—Type of ground color of the fruit is yellow, type of over color of skin of the fruit is deep red, with medium intensity and medium amount, form of over color of skin of the fruit is distinguished stripe.

*Russet.*—Position of russet of the fruit is on cheeks, with moderate amount, raised russet lenticels of the fruit is present, size of lenticels of the fruit is medium and is similar to that of the parent tree "Fuji" and number of lenticels of the fruit is medium.

*Skin.*—Shininess of skin of the fruit is weak, greasiness of skin of the fruit is weak, bloom and cracking tendency of skin of the fruit is absent, surface texture of the skin of the fruit is moderate, length of stalk of the fruit is medium (2.2 cm), thickness of stalk of the fruit is stout (thicker than that of the parent tree "Fuji"), distinct swelling at end of stalk of the fruit is present.

*Core.*—Shape of core of the fruit is oval, and size of core of the fruit is medium.

*Flesh.*—Color of flesh of the fruit of this tree is yellowish white, juiciness of the flesh is very juicy, medium sweet (Brix 14.0), acidity of the flesh if weak, firmness of the flesh is firm, and easy bruising of the flesh is medium. Texture of the flesh is coarse, water core of mature fruit is medium, astringency of the flesh is absent, flavor of the flesh is weak.

*Seed.*—Number of fully developed seeds of this tree are few, shape of the seed is obovate and size of the seed is medium.

Physiological and ecological characteristics:

*Harvest season.*—Time of fruit ripening for eating is late, early November, on original tree, and is similar to or later than that of the parent tree "Fuji". Early drop and preharvest drop of fruit of this tree are absent or slight, and physiological disorder of the fruit is few.

*Storage.*—Keeping quality of fruit of this tree at ordinary storage and cold storage are very long respectively. Storage life of this fruit is very long, as same as that of the parent tree "Fuji".

*Disease resistance.*—Occurrence of Core rot of the fruit is absent or weak.

*Use.*—The fruit of this tree is useful and good as dessert apple.

*Productivity.*—Tree of this variety is regularly productive and needs adequate fruit thinning.

It has been ascertained that the claimed tree "Tensei" is a tetraploid (4n=68), although the parent tree "Fuji" is a diploid. It is rare that the tetraploid variety is derived from the diploid variety of apple tree "Fuji" as a bud mutant.

There are differences in the type of ground color and type of over color of skin of the fruit of the claimed tree as compared to that of the parent tree "Fuji". The type of ground color of the fruit of the claimed tree is yellow, but that of the parent tree is soft yellow green (3109), and the type of cover color of skin of the fruit of the claimed tree is deep red or purplish red, but that of the parent is deep red.

Form of cover color of skin of the fruit of the claimed tree is strip (distinguished strip) and is similar to that of the parent tree practically. Amount of color of skin of the fruit of the claimed tree is medium (50%) present) and is similar to that of the parent tree practically.

Shininess of skin of the fruit of the claimed tree is weak and is similar to that of the parent tree practically. Bloom of skin of the fruit of the claimed tree is absent and is similar to that of the parent tree. Surface texture of the skin of the fruit of the claimed tree is moderate and is similar to that of the parent tree.

Date of coloring of the fruit of the claimed tree is late as compared to that of the parent tree.

Pubescence of the one-year-old shoot of the claimed tree is weak and is similar to that of the parent tree. Thickness of the one-year-old shoot of the claimed tree is thick (stout), but that of the parent tree is thin (slender). Length of internode of the one-year-old shoot of the claimed tree is medium (2.1–2.5 cm) and is similar to that of the parent tree. Size of lenticels of one-year-old shoot of the claimed tree is medium, but that of the parent tree is small.

Number of lenticels of one-year-old shoot of the claimed tree is much (numerous) and is similar to that of the parent tree.

Size of fruit of the claimed tree is very large (the length of fruit: 8.83 cm, breadth of fruit: 9.76 cm, weight: 496 g), but that of the parent tree is large (the length of fruit: 8.36 cm, breadth of fruit: 8.88 cm, weight: 352 g). Data was based on the average size of the typical fruit of each tree.

In regard to the time of fruit ripening for eating, that of the claimed tree is similar to or later than that of the parent tree.

Sweetness of the flesh of the fruit of the claimed tree is medium (about 14% by refractometer) and similar to that of the parent tree.

As to pollination requirements, the claimed tree requires cross-pollination in the same way as the parent tree practically.

As to the size of leaf, the length of lamina (L) and the breadth of leaf (B) of the claimed tree are 7.86 cm and 6.41 cm respectively, but that of the parent tree are 8.11 cm and 5.52 cm respectively. L/B ratio of the claimed tree is 1.23, but that of the parent tree is 1.47. Data was based on the average size of the typical leaf of each tree.

Size of opened flower of the claimed tree is large, but that of the parent tree is medium.

Further, there are differences in shape of fruit, crowning at eye end, aperture of eye, breadth of basin, length of stalk and thickness of stalk of the fruit of the claimed tree as compared to that of the parent tree. Shape of fruit of the claimed tree is round, but that of the parent tree is oval.

Crowning at eye end of the fruit of the claimed tree is medium, but that of the parent tree is absent or weak.

Aperture of eye of the fruit of the claimed tree is open, but that of the parent tree is closed. Breath of basin of the fruit of the claimed tree is broad, but that of the parent tree is medium.

Length of stalk of the fruit of the claimed tree is medium (2.2 cm), but that of the parent tree is long (2.5 cm). Thickness of stalk of the fruit of the claimed tree is thick (stout 0.32 cm), but that of the parent tree is medium (0.26 cm). Each data was based on the average size of the typical fruit of each tree.

Furthermore, there are differences in colors of unopened flower, size of sepal and size of anthers of the claimed tree as compared to that of the parent tree.

Color of unopened flower is purplish pink (9503), but that of the parent tree is light purplish pink (9502).

Size of sepal of the claimed tree is large, but that of the parent tree is small.

Size of anthers of the flower of the claimed tree is large, but that of the parent tree is small.

In particular, "Tensei" of the present invention is distinguished from known "Fuji", "Yataka", and "Benishogun" by its characteristics that size of opened flower of the new apple tree is large, shape of fruit of the tree is round, crowning at eye end of the fruit is medium, aperture of eye of the fruit is open, breadth of basin of the fruit is broad and the like.

General Observations

The coloration of the bark, foliage and ripened fruit of "Tensei" and "Fuji" is widely variable in range and the ranges generally overlap. Coloration of flower buds just prior to opening may be seen to differ, with those of "Tensei" having darker shades of purplish-pink, near RHSCC 62C to RHSCC 63D, while the shades of buds of "Fuji" are not generally darker than about RHSCC 65C. Ground color of fruit in late mid-season before fruit takes on red colors also differs, with that of "Tensei" being a deeper green of about RHSCC 149C while that of "Fuji" is a soft yellow green near RHSCC 45D. The ripe fruit of each tree is red stripped near RHSCC 45D. The ripe fruit of each tree is red stripped over varying shades of ground color, which may or may not be over-colored by varied intensities of a solid red blush which forms as a function of exposure to sunlight.

What is claimed:

1. A new and distinct variety of apple tree, substantially as illustrated and described herein, to be a true mutation of the parent cultivar "Fuji", particularly characterized by its fruit, opened flower and leaf which are larger than the known "Fuji variety".

* * * * *

HOKUTO

BUD MUTATION OF FUJI

FUJI

DATE OF THE PHOTO
DECEMBER 10, 1989

BUD MUTATION OF FUJI

DATE OF THE PHOTO
DECEMBER 10, 1989